United States Patent
Therin et al.

(10) Patent No.: US 6,596,002 B2
(45) Date of Patent: Jul. 22, 2003

(54) ABDOMINAL WALL REINFORCEMENT FOR THE TREATMENT OF INGUINAL HERNIAS BY AN ANTERIOR ROUTE

(75) Inventors: Michel Therin, Lyons (FR); Philippe Chastan, Bordeaux (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/838,290

(22) Filed: Apr. 20, 2001

(65) Prior Publication Data

US 2002/0013590 A1 Jan. 31, 2002

(30) Foreign Application Priority Data

Apr. 20, 2000 (FR) .............................. 00 05123

(51) Int. Cl.[7] .................................. A61F 2/02
(52) U.S. Cl. ...................... 606/151; 606/113; 606/114; 606/127; 606/200; 623/11; 128/899; 602/58
(58) Field of Search ............... 60/1, 113, 114, 60/127, 151, 110, 200, 213; 623/11; 128/899; 602/58

(56) References Cited

U.S. PATENT DOCUMENTS

| 5,147,374 A | * | 9/1992 | Fernandez ............... 606/151 |
| 5,356,432 A |   | 10/1994 | Rutkow et al. |
| 5,368,549 A | * | 11/1994 | McVicker |
| 5,569,273 A |   | 10/1996 | Titone et al. |
| 5,716,409 A | * | 2/1998 | Debbas |
| 5,824,082 A | * | 10/1998 | Brown ..................... 623/11.11 |
| 6,042,534 A | * | 3/2000 | Gellman et al. ............. 600/30 |
| 6,066,776 A | * | 5/2000 | Goodwin et al. ........... 606/151 |
| 6,174,320 B1 | * | 1/2001 | Kugel et al. ................ 606/151 |
| 6,241,768 B1 | * | 6/2001 | Agarwal et al. ............ 606/151 |
| 6,258,124 B1 | * | 7/2001 | Darois et al. ............... 606/151 |
| 6,383,201 B1 | * | 5/2002 | Dong ......................... 606/151 |
| 6,408,656 B1 | * | 6/2002 | Ory et al. .................... 66/170 |

FOREIGN PATENT DOCUMENTS

| DE | A1 198 32 634 | * | 1/2000 |
| EP | A1 0 719 527 | * | 7/1996 |
| EP | 0 797 962 A2 | | 10/1997 |
| EP | 0 827 724 A2 | | 3/1998 |
| EP | 0 836 838 A1 | | 4/1998 |
| FR | A 2 744 906 | * | 8/1997 |
| FR | A 2 766 698 | * | 2/1999 |
| WO | WO 95/07666 | | 3/1995 |
| WO | WO 96/03091 | | 2/1996 |
| WO | WO 96/09795 | * | 4/1996 |
| WO | WO 96/14805 | * | 5/1996 |
| WO | WO 96/41588 | | 12/1996 |

* cited by examiner

*Primary Examiner*—Gregory L. Huson
*Assistant Examiner*—Azy Kokabi
(74) *Attorney, Agent, or Firm*—Oliff & Berridge, PLC

(57) ABSTRACT

This reinforcement consists of a reinforcement piece (2) and of a flap (3) connected to this reinforcement piece (2); the reinforcement piece (2) is made of a prosthetic knit and has a slit (5) for its engagement around the spermatic cord; the flap (3) is able to be folded over the slit (5).

13 Claims, 4 Drawing Sheets

7 6 5 4 3 2 1 0

Figure 1:
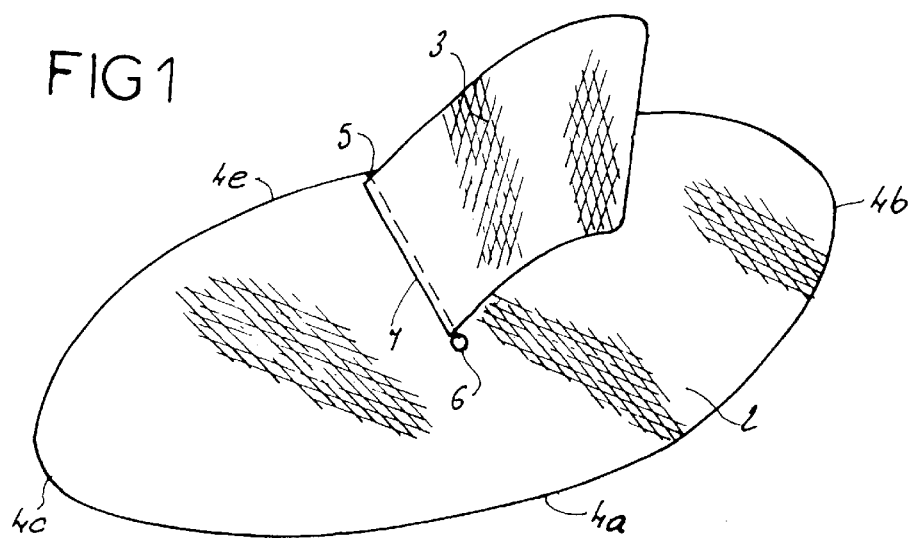

ABDOMINAL WALL REINFORCEMENT FOR THE TREATMENT OF INGUINAL HERNIAS BY AN ANTERIOR ROUTE

The invention relates to an abdominal wall reinforcement for the treatment of inguinal hernias by an anterior route and without tension.

In the treatment of parietal insufficiencies (hernias and eventrations for the most part), the aim of reinforcement is to give a permanent mechanical support to the surgical reconstruction. The reinforcement is all the more effective, and its local tolerance all the better, if it integrates in the tissue intimately and at an early stage. To achieve intimate and early integration without formation of a peripheral fibrous shell, the macroporosities of the implant must be as widely open as possible to the outside and the elasticity of the reinforcement must allow it to follow the physiological deformations of the wall. The limits are fixed by the mechanical resistance of the textile, which must be greater than 10 decanewtons in the standardized ISO5081 test, by the maneuverability by the surgeon, and by the impossibility of hernia recurring through the pores of the tissue which must be a maximum of 7 to 10 millimeters in diameter.

The concept of a tissue reinforcement of the abdominal wall in the form of a knitted textile has been known for decades in the scientific literature. A number of technical solutions have been described, in particular in the following documents: U.S. Pat. No. 5,569,273, WO 96/03091, EP 0,797,962, FR 2,766,698. These all have in common the knitting of monofilaments or multifilaments of polypropylene or polyester.

In a known manner, such tissue reinforcements have to meet a number of requirements, and in particular they have to have a mechanical strength in all directions, be biocompatible, flexible and conformable, while having a certain elasticity, be porous and transparent, be able to be sutured and recut, while at the same time being non-tear and runproof, and, finally, they must be sterilizable and durable. In general, these reinforcements are knitted and made up of several sheets of interlaced yarns.

Specific forms of these textiles which are able to conform, on the one hand, to the anatomy of the inguinal region and, on the other hand, to the surgical technique employed have also been known for many years, both for posterior access routes (EP 0,836,838, WO 95/07666, WO 96/41588) and for anterior access routes (U.S. Pat. No. 5,356,432, EP 0,827,724). While in general the reinforcements designed for the posterior access routes are of large dimensions and require only a small number of fixing points, the reinforcements designed for the anterior access routes are of smaller dimensions, are slotted (in advance or extemporaneously) to surround the spermatic cord and therefore require relatively extensive fixing, on the one hand in order to close the slit on itself, and on the other hand to oppose the intra-abdominal forces of extrusion and, finally, to guarantee rapid integration with the peripheral tissues.

The present invention relates to a novel type of knitted reinforcement specially adapted to the treatment of inguinal hernias by an anterior access route and placed in a premuscular location, affording ease and speed of use, securing of its position by the practitioner, and effective functional repair for the patient.

This reinforcement consists of a reinforcement piece and of a flap connected to this reinforcement piece; the reinforcement piece is made of an openworked prosthetic knit consisting at least partially of multifilament yarns and has a slit for its engagement around the spermatic cord; this prosthetic knit can in particular be that described in French Patent No. 2,766,698; the flap is able to be folded over the slit.

According to the invention, the flap is shaped in the form of a sector of a circular annulus and is connected via one of its radial edges to one of the edges of the reinforcement piece which delimits the slit, the shape of the flap being such that the flap, when folded over said slit, is inscribed on the medial half of the reinforcement piece, without protruding beyond the edge thereof.

The connection of the flap to one of the edges of the reinforcement piece which delimits the slit makes it possible to perfectly secure the flap to the reinforcement piece and to perfectly maintain this same edge of the reinforcement piece after the reinforcement has been put into place.

The abovementioned shape of the flap, in the form of a sector of a circular annulus, allows the flap to have a large surface area in contact with the reinforcement piece, for a perfect connection of this flap to this piece; this shape at the same time ensures that the inner arched edge of the flap does not interfere with the spermatic cord and that the outer arched edge of this flap does not extend beyond the edge of the reinforcement piece, towards the outside thereof, and therefore does not interfere with the surrounding tissues.

This shape of the flap additionally favors folding of this flap against the reinforcement piece once the reinforcement is in position.

The radius of the circle in which the flap is inscribed can be from 80 to 100 mm, in particular 90 mm.

According to a preferred embodiment, the reinforcement has the general shape of an ellipse, comprising a lower edge with a large radius of curvature which is able to match the crural arch as far as the pubis, two ends with a small radius of curvature, and an upper edge with rectilinear parts and a curved part, while the slit, arranged in the upper part and substantially halfway along the length of the upper edge, perpendicular to its rectilinear edge, opens via its inner end into a circular orifice for lodging the spermatic cord and securing the reinforcement.

This reinforcement satisfies the traditional requirements of the wall reinforcements mentioned above and, by virtue of its particular shape, widely covers all the zones of potential weakness, while at the same time being easy to put into place.

The upper position of the slit facilitates the deployment of the lateral parts of the reinforcement under the aponeurosis of the greater oblique muscle. The circular orifice receiving the spermatic cord suppresses all shearing stresses on this cord and improves the positioning and securing of the reinforcement.

The flap, on its face which is to be folded over the reinforcement piece, preferably comprises means, integral therewith or attached to it, for fastening or joining to the knitted structure of the reinforcement piece, for example grip means.

In one embodiment, the flap is made of a prosthetic knit satisfying the requirements set out above and comprising, projecting from its face which is to be folded over the reinforcement piece, spiked naps formed by a monofilament yarn and having a length allowing them to penetrate into and attach themselves in the knitted structure of the reinforcement piece without protruding from the latter.

Depending on the applications, this monofilament yarn is made of biocompatible polymer or of bioabsorbable material.

Once the flap has been folded over the reinforcement, the spiked naps engage in and between the multifilament yarns of the knit of the reinforcement, which ensures that the flap is locked in position. This locking, effective even in a liquid environment, is sufficient to secure the closure of the slit and offer mechanical resistance to the tangential stresses, while permitting the flap to be unfastened by traction in order to adjust its position.

The density of the spiked naps is determined as a function of the prosthetic knits used but is between 50 and 90 naps per cm².

Likewise, the length of the naps, measured from the base projecting from the attachment sheet to the top of the spike, depends on the thickness of the prosthetic knit forming the reinforcement piece, but is between 1 and 2 millimeters.

The reinforcement piece itself can comprise means, integral therewith or attached to it, for fastening or joining, for example grip means, projecting from one and/or the other of its main faces, these fastening or joining means being able to permit the fastening or joining of this reinforcement piece to the tissues in contact with which this reinforcement piece is intended to be placed.

These fastening or joining means can have a structure identical to that, described above, of the means for fastening or joining the flap to the reinforcement piece.

The knit from which the reinforcement piece is made can be of the "flat knit" type or can have two porous layers connected by connecting yarns, the weave forming runproof transverse channels opening out from the two porous layers.

Other characteristics and advantages will become evident from the following description in which reference is made to the attached diagrammatic drawing representing, by way of example, an embodiment of the parietal reinforcement according to the invention.

Figure 2:
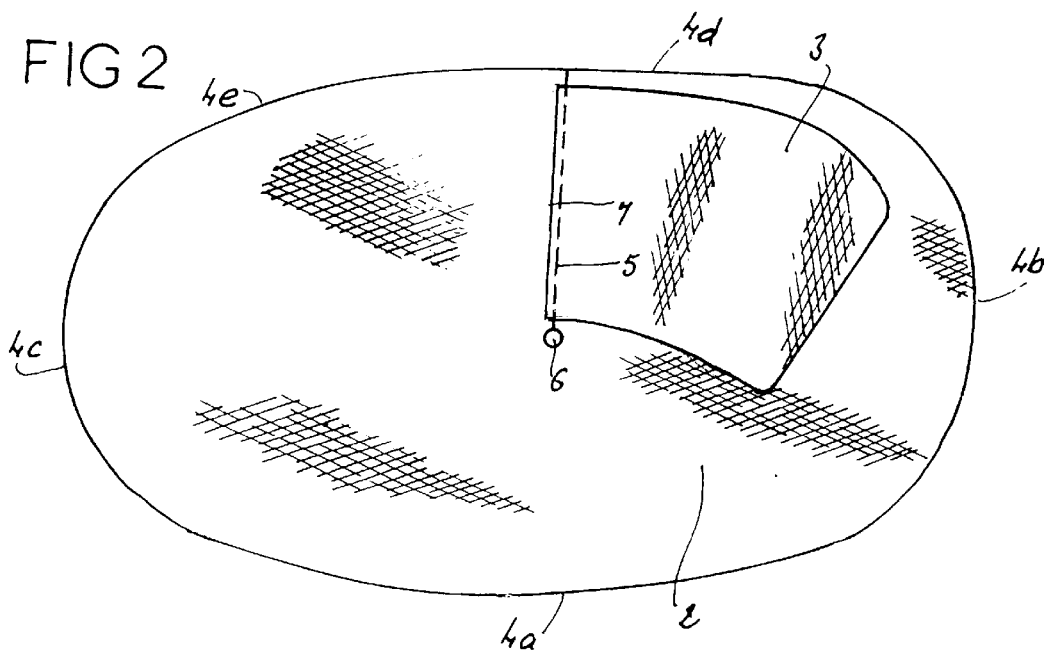
Figure 6:
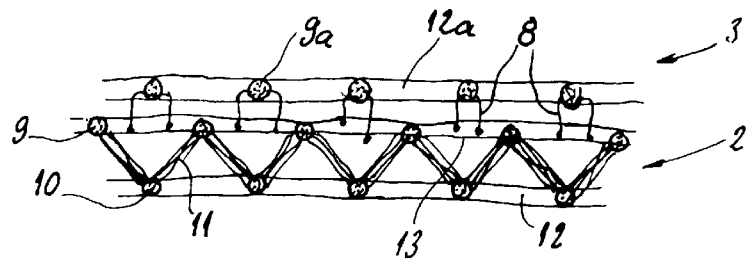
Figure 3:
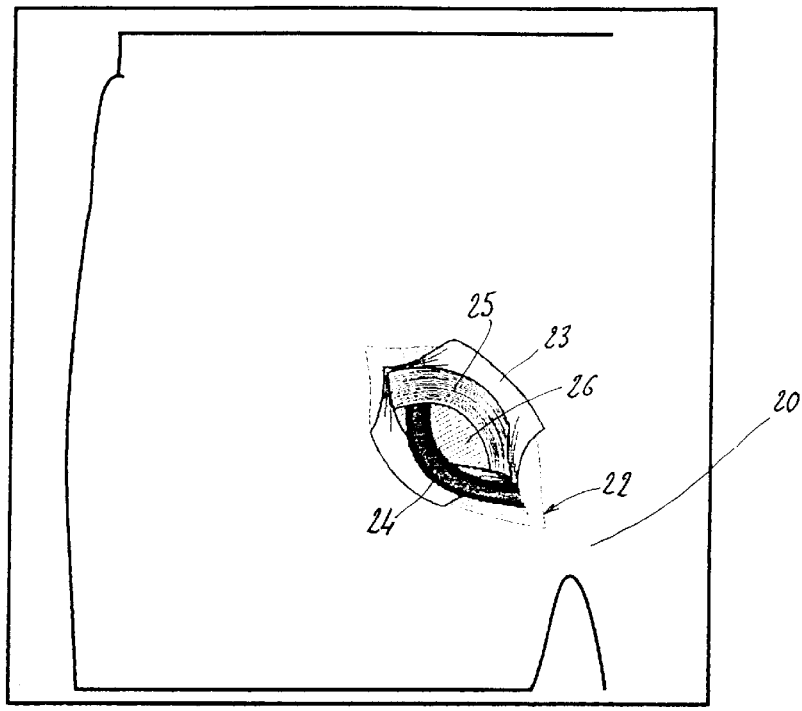
Figure 4:
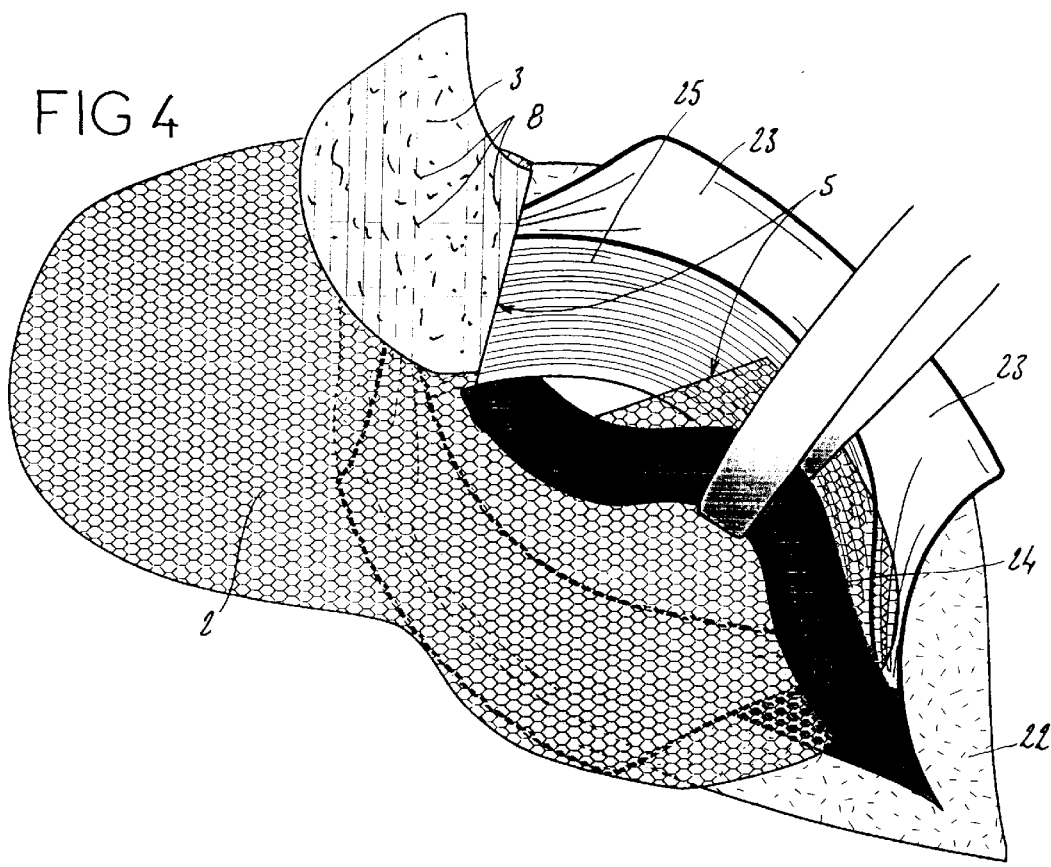
Figure 5:
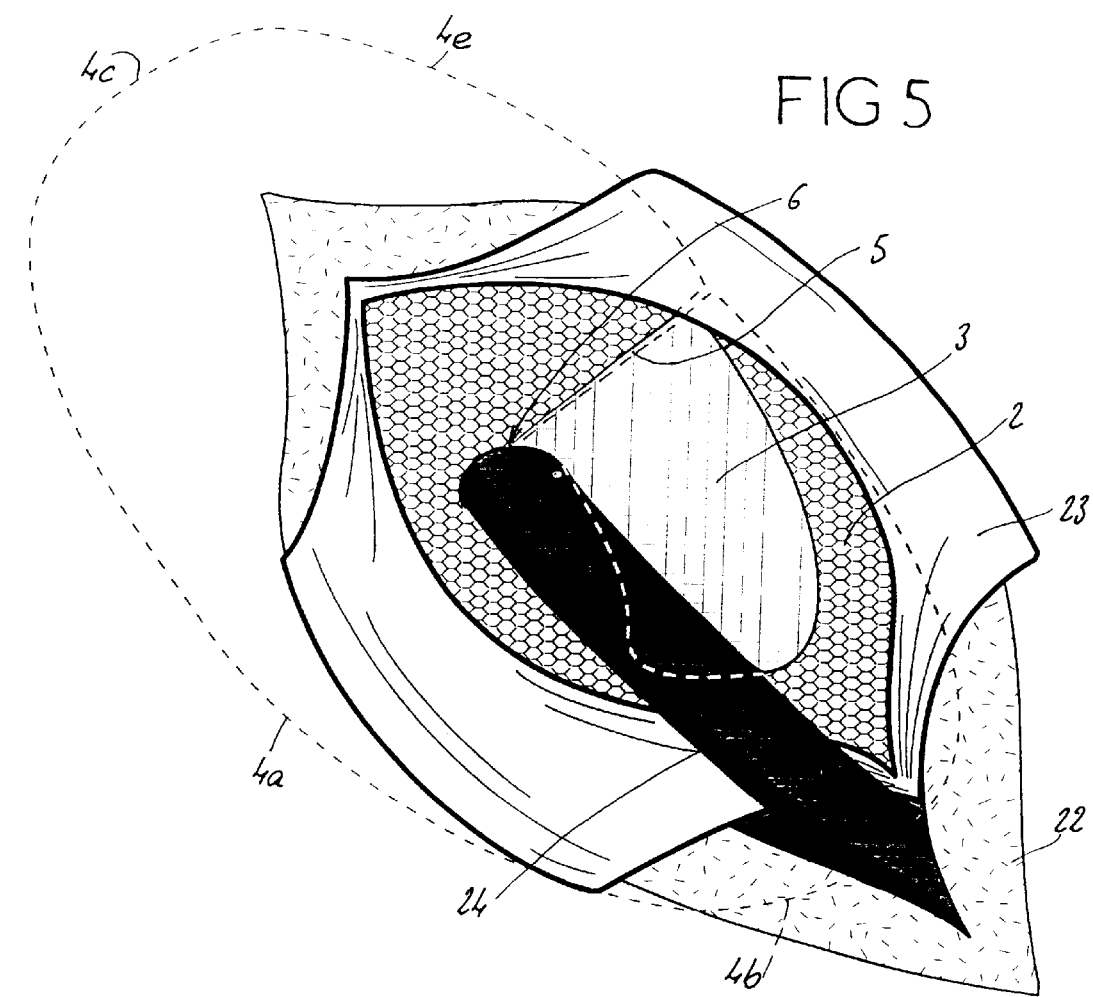
Figure 7:
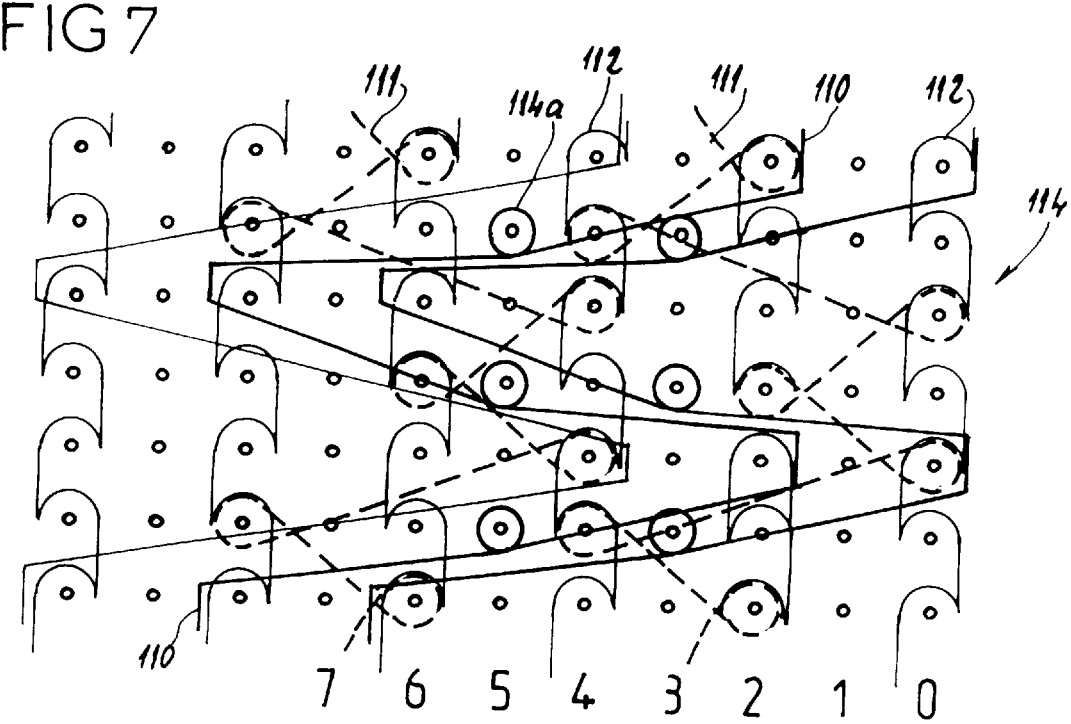
Figure 8:
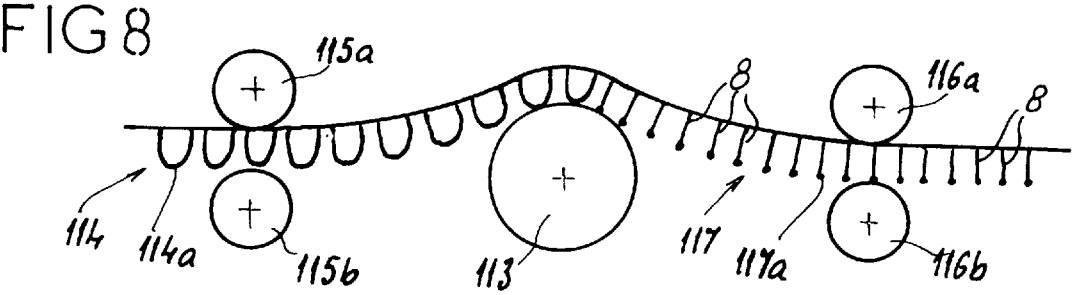

FIG. 1 is a perspective view of the reinforcement when its flap is in the course of being folded over, FIG. 2 is a plan view when its flap has been folded over the reinforcement piece, FIG. 3 is a partial plan view of the treatment of a hernia, just after skeletization of the spermatic cord, FIGS. 4 and 5 are views, on an enlarged scale compared with FIG. 3, showing the positioning of the reinforcement and the reinforcement piece before fixation of the flap, FIG. 6 is a diagrammatic side view illustrating, in a nonconventional manner, the knitted structures of the reinforcement piece and of the flap, respectively, FIG. 7 is a diagram representing, by way of example, the weave of the three sheets of a grip-type knit by means of which it is possible, after thermal treatment according to FIG. 7, to obtain a flap with spiked naps, and FIG. 8 is a diagrammatic side view of a device with which it is possible to form the spiked naps.

The figures show a reinforcement of the abdominal wall for the treatment of inguinal hernias by an anterior route and without tension.

This reinforcement consists of a reinforcement piece 2 and of a flap 3 connected to this reinforcement piece 2.

The reinforcement piece 2 is made of a knit which satisfies the requirements of the prosthetic knits mentioned in the preamble of the present description. In one embodiment, this knit is three-dimensional and openworked, with two porous faces connected by connecting yarns, and for example is made in the knit defined in French Patent No. 2,766,698.

As is shown in FIG. 2, the reinforcement piece 2 has, viewed from above, the general shape of an ellipse. This ellipse includes a lower edge 4a with a large radius of curvature, two lateral edges 4b, 4c with a small radius of curvature, and an upper edge made up of a rectilinear part 4d and of a part with a large radius of curvature 4e. This shape of the upper edge is specifically adapted to the anterior inguinal region and more precisely to the space formed after opening of the aponeurosis of the external oblique muscle, access to the conjoined tendon and the aponeurosis of the rectus muscle, the latter being fixed between the insertion of the aponeurosis of the external oblique muscle and that of the rectus muscle. This anatomical asymmetry combined with the presence of the flap 3 means that there is a right reinforcement and a left reinforcement, the reinforcement shown being a right reinforcement (relative to the patient). The large curvature 4a of the lower edge allows a perfect match to the crural arch as far as the pubis.

This reinforcement has, substantially halfway along the length of its upper edge 4d–4e, a slit 5 perpendicular to the rectilinear edge 4d and extending substantially over half of the width. The inner end of this slit 5 opens into an orifice 6 which is cylindrical and which, for example, has a diameter of 3 to 7 millimeters.

The flap 3 has a shape of a sector of a circular annulus and is connected via one of its radial edges to one of the edges of the reinforcement piece 2 which delimits the slit 5. It extends over a surface several times smaller than that of the reinforcement piece 2 and is inscribed in a circle of 90 mm radius.

The flap 3 is joined to the piece 2 in such a way that the concavity of its inner and outer arched edges is directed towards the orifice 6.

The flap 3 is composed of an openworked runproof prosthetic knit made, for example, of multifilament synthetic yarns of polyester. It is joined to the reinforcement by a longitudinal stitch or seam 7 parallel and adjacent to one of the edges of the piece 2 which delimits the slit 5. The knit of this flap also comprises a monofilament yarn forming spiked naps 8 projecting from one of its faces.

Depending on the applications, this yarn is made of biocompatible polymer, such as polypropylene, or bioabsorbable material chosen, for example, from the group comprising the polymers of p-dioxanone, polyglycolides, polyorthoesters, polymers of trimethylene carbonate, stereo-copolymers of L-lactic acid and D-lactic acid, homopolymers of L-lactic acid, copolymers of lactic acid and a compatible comonomer, such as derivatives of alpha-hydroxy acids.

These spiked naps 8 have a length sufficient to penetrate into the meshes and between the filaments of the yarns of the knitted structure of the reinforcement piece 2, by simple pressure, but insufficient to totally pass through this structure. By way of example, for prosthetic knits having a thickness of between 1.5 and 2.2 millimeters, the length of the naps measured from their base, projecting from one of the faces of the knit, to the summit of the spike is between 1 and 2 millimeters.

FIG. 6 is a diagrammatic illustration of the knitted structures of the reinforcement piece 2 and of the flap 3. In this figure, reference numbers 9 and 10 designate the multifilament polyester yarns defining the two porous sheets of the reinforcement 2, reference number 11 designates the multifilament yarns providing for the connection between the two sheets and giving the tissue its three-dimensional character 3, reference numbers 12 and 13 designate the cells defined by the meshes and giving porosity and transparency to the sheet. This figure also shows that the knit of the flap 3 also comprises spiked naps 8 which project from one of its faces and are able to penetrate and insert themselves in the meshes and between the filaments of the meshes when the flap 3 is applied on the reinforcement piece 2.

The density of the spiked naps 8 depends on the weaves and the yarns used to form the knitted structures 2 and 3, but it is generally between 50 and 90 naps per cm².

The reinforcement piece 2 and the flap 3 are supplied in the state shown in FIG. 2 but with the flap 3 folded under the piece 2 in such a way that its spikes project from its face opposite the one coming into contact with this piece 2.

The flap 3 can be obtained or fashioned from a grip-type knit obtained, for example, by a method described below with reference to FIGS. 7 and 8.

The grip-type knit is made on a warp knitting machine, of the tricot or Raschel type, with at least three sheets or warps of yarn and as many guide bars, as is shown in FIG. 7.

The rear bar is threaded, one guide full and one guide empty, with monofilament of biocompatible and hot-melt polymer, for example polypropylene, having a diameter of over 0.10 millimeter. In practice, this diameter is between 0.14 and 0.18 millimeter and is of the order of 0.15 millimeter. This yarn is represented by reference number 110 and in a solid line in FIG. 7.

The intermediate bar is threaded, one guide full, three guides empty, with multifilament polyester, but it can also be threaded with monofilament polyester or monofilament or multifilament polypropylene. This yarn is represented by a broken line and by reference number 111 in FIG. 7. The intermediate bar works in such a way as to obtain a zigzag openwork pattern between the columns of meshes.

Finally, the front bar is threaded, one guide full, one guide empty, and works in chain weave with a multifilament or monofilament yarn of polyester or polypropylene and, for example, a multifilament polyester yarn. This yarn is represented by a thin line and by reference number 112 in FIG. 7. The chain stitch imprisons the monofilament 110 and maintains the knit in length while contributing to the formation of the knit with the intermediate sheet formed by the yarn 111. The different yarns are worked according to the following chart:

| Warp > | Rear bar I | Intermediate bar II | Front bar III | < Raschel |
|---|---|---|---|---|
|  | 7 | 3 | 1 |  |
|  | 7 | 2 | 0 |  |
|  | — | — | — |  |
|  | 3 | 4 | 0 |  |
|  | 4 | 5 | 1 |  |
|  | — | — | — |  |
|  | 0 | 1 |  |  |
|  | 0 | 0 |  |  |
|  | — | — |  |  |
|  | 4 | 2 |  |  |
|  | 3 | 3 |  |  |
|  |  | — |  |  |
|  |  | 1 |  |  |
|  |  | 0 |  |  |
|  |  | — |  |  |
|  |  | 4 |  |  |
|  |  | 5 |  |  |

The rear bar places the yarn in partial weft under the chain stitch and "thrown" onto the needle not forming a chain stitch. For this reason, at the next row, the needle not forming a chain stitch not being supplied permits escape of the monofilament mesh which forms a loop 114a projecting from the front face of the knit.

The threading—one guide full, three guides empty—in the intermediate bar, associated with the displacement, makes it possible to form a light ground texture, stable in width, and openworked to permit good tissue integration.

The knit 114 thus obtained is provided with loops 114a (FIG. 8) which are perpendicular to one of its faces and of which the rigidity and the hold at a right angle are obtained by the rigidity or nerve of the monofilament employed. This rigidity is necessary for the subsequent formation of the spiked naps which ensure the grip function.

In another embodiment, the monofilament forming the loops and subsequently the spiked naps is made of bioabsorbable hot-melt material chosen, for example, from the group consisting of the polymers of p-dioxanone, polyglycolides, polyorthoesters, polymers of trimethylene carbonate, stereocopolymers of L-lactic acid and D-lactic acid, homopolymers of L-lactic acid, copolymers of lactic acid and a compatible comonomer, such as derivatives of alpha-hydroxy acids.

On leaving the loom, the knit 114 is subjected to a thermosetting operation which stabilizes it in length and in width, then it is subjected to a phase of formation of the spiked naps 8 consisting, as is shown in FIG. 8, in passing it over a cylinder 113 containing an electrical heating resistor. The knit 114 is pressed flat on the cylinder 113 by two pairs of rollers, upstream 115a, 115b and downstream 116a, 116b, respectively, which are vertically displaceable for controlling this pressing force.

This control as well as that of the temperature of the resistor placed in the cylinder 113 and of the speed of the knit 114 across the cylinder make it possible to melt the head of each of the loops 114a to form a nap 117 comprising at its end a mushroom or spike 117a. The length S of the spiked naps 8, measured from the face from which they project perpendicularly as far as the summit of the spike, is determined such that it is smaller than the thickness E of the knitted structure in which they are to penetrate and fasten themselves, and it is between 1 and 2 millimeters.

Depending on the applications, the knitted structure of the reinforcement piece 2 may or may not be coated with any material promoting tissue integration and/or local tolerance.

The shape of the reinforcement piece 2 makes it possible, with two reinforcements of different sizes, of homothetic shapes, to widely cover all the potentially weak zones of the abdominal wall in the inguinal region, that is to say both the median direct orifice and the lateral indirect orifice, whatever the size of the patient.

The conditions for implanting this reinforcement will now be described with reference to FIGS. 3 to 5.

In FIG. 3, reference number 20 designates a patient's groin in which the surgeon has made a skin incision 22 of the order of 5 to 8 centimeters, an incision of the aponeurosis of the external oblique muscle 23, represented in the reclined position, has proceeded to skeletize the spermatic cord 24, identified and forced back the hernial sac in its trajectory, identified and dissected the margin of the internal oblique muscle 25 and the transversalis fascia 26.

This then is the conventional technique for accessing inguinal hernias with a view to treating them by an anterior route with placement of a reinforcement.

In a subsequent phase of implantation, shown in FIG. 4, the surgeon performs the following maneuvers:

presentation of the reinforcement with the slit 5 upwards and the flap 3 open, engagement of the slit 5 around the cord 24, deployment of the large curvature of the reinforcement piece 2 such that it matches the crural arch (inguinal ligament), complete deployment of the reinforcement piece 2, the latter being perfectly centered by positioning the cord in the orifice 6 so as to cover all the potential zones of weakness.

At the end of this phase of positioning, and as is shown in FIG. 5, the flap 3 is folded over so as to straddle the slit 5 and so that its spiked naps 8 grip in the knitted structure of the reinforcement piece 2, thereby securing the closure of the slit 5. After adjusting the deployment of the reinforcement piece 2, it is possible to proceed to unfasten the flap 3 so as to adjust its position in order to ensure good closure of the slit 5 and a good connection of the piece 2 and flap 3, without formation of folds, and without exerting any stress on the cord 24.

The shape of the flap 3 allows it to have a large surface area in contact with the piece 2 and the inner arched edge of this flap does not interfere with the spermatic cord. The outer arched edge of the flap 3 for its part does not extend beyond the edge of the reinforcement piece 2, towards the outside thereof, and therefore does not interfere with the surrounding tissues.

The next phase then involves conventional fixing of the reinforcement piece 2 to the surrounding tissues by means of clips or continuous or discontinuous sutures, to the pubis at the infero-median angle, to the lower margin of the inguinal ligament (crural arch), to the upper margin of the aponeurosis of the rectus muscle (abdominal wall).

If appropriate, a suture point can be placed on the slit 5 in order to adjust the size of the orifice surrounding the cord 24.

Treatment is completed by suturing the aponeurosis of the external oblique muscle and closing the skin.

The reinforcement according to the invention thus has the following advantages:

- anatomical shape widely covering all the potential zones of weakness,
- positioning simplified by means of the presence of the flap,
- reduced and simplified fixing by virtue of the self-fastening nature of the flap on the reinforcement piece,
- as the fastening is reversible, adjustment of the closure of the slit can be repeated several times,
- the self-fastening nature of the flap limits the closure of the slit around the cord to a maximum optional point,
- the upper position of the slit facilitates the deployment of the lateral part of the reinforcement under the aponeurosis of the greater oblique muscle,
- the folding of the flap 3 on the reinforcement piece 2 generates a local double thickness precisely at the weakest point of the inguinal region, that is to say opposite the transversalis fascia, thereby reinforcing the arrangement.

What is claimed is:

1. An abdominal wall reinforcement for the treatment of inguinal hernias by an anterior route, consisting of a reinforcement piece (2) and of a flap (3) connected to this reinforcement piece (2); the reinforcement piece (2) is made of an openworked prosthetic knit consisting at least partially of multifilament yarns and has a slit (5) for its engagement around the spermatic cord; the flap (3) is able to be folded over the slit (5);

said reinforcement being distinguished in that the flap (3) is shaped in the form of a sector of a circular annulus and is connected via one of its radial edges to one of the edges of the reinforcement piece (2) which delimits the slit (5), the shape of the flap (3) being such that the flap (3), when folded over said slit (5), is inscribed on the medial half of the reinforcement piece (2), without protruding beyond the edge thereof.

2. The reinforcement as claimed in claim 1, wherein the radius of the circle in which the flap (3) is inscribed is between 80 and 100 mm, and is in particular 90 mm.

3. The reinforcement as claimed in claim 1, wherein the reinforcement piece (2) has the general shape of an ellipse, comprising a lower edge (4a) with a large radius of curvature which is able to match the crural arch as far as the pubis, two ends (4b, 4c) with a small radius of curvature, and an upper edge (4d, 4e) with rectilinear parts (4d) and a curved part (4e), while the slit (5), arranged in the upper part and substantially halfway along the length of the upper edge, perpendicular to its rectilinear edge (4d), opens via its inner end into a circular orifice (6) for lodging the spermatic cord and securing the reinforcement (2).

4. The reinforcement as claimed in claim 1, wherein the flap (3), on its face which is to be folded over the reinforcement piece (2), comprises means, integral therewith or attached to it, for fastening or joining to the knitted structure of the reinforcement piece (2), for example grip means.

5. The reinforcement as claimed in claim 4, wherein the flap (3) is made of a prosthetic knit, openworked and runproof, and having, projecting from its face which is to be folded over the reinforcement piece (2), spiked naps (8) formed by a monofilament yarn and having a length allowing them to penetrate in a limited manner into the knitted structure of the reinforcement piece (2), without protruding from the latter.

6. The reinforcement as claimed in claim 5, wherein the density of the spiked naps (8) is between 50 and 90 per cm2.

7. The reinforcement as claimed in claim 5, wherein the length of the spiked naps (8) is between 1 and 2 millimeters.

8. The reinforcement as claimed in claim 5, wherein the monofilament yarn forming the spiked naps (8) is made of polypropylene.

9. The reinforcement as claimed in claim 5, wherein the monofilament yarn forming the spiked naps (8) is made of bioabsorbable material chosen from the group consisting of the polymers of p-dioxanone, polyglycolides, polyorthoesters, polymers of trimethylene carbonate, stereo-copolymers of L-lactic acid and D-lactic acid, homopolymers of L-lactic acid, copolymers of lactic acid and a compatible comonomer, such as derivatives of alpha-hydroxy acids.

10. The reinforcement as claimed in claim 1, wherein the reinforcement piece comprises means, integral therewith or attached to it, for fastening or joining, protruding from one and/or the other of its main faces, these fastening or joining means being able to permit the fastening or joining of this reinforcement piece to the tissues in contact with which this reinforcement piece is intended to be placed.

11. The reinforcement as claimed in claim 10, wherein the fastening or joining means of the reinforcement piece have a structure identical to that of the means for fastening or joining the flap to the reinforcement piece.

12. The reinforcement as claimed in claim 1, wherein the knit from which the reinforcement piece is made has two porous layers connected by connecting yams, the weave forming runproof transverse channels opening out from the two porous layers.

13. The reinforcement as claimed in claim 10, wherein said means is a grip means.

* * * * *